United States Patent [19]

Rosen et al.

[11] Patent Number: 5,556,767
[45] Date of Patent: Sep. 17, 1996

[54] POLYNUCLEOTIDE ENCODING MACROPHAGE INFLAMMATORY PROTEIN γ

[75] Inventors: Craig A. Rosen, Laytonsville; Haodong Li, Germantown; Steven Ruben, Olney; Mark D. Adams, North Potomac, all of Md.

[73] Assignee: Human Genome Sciences, Inc., Rockville, Md.

[21] Appl. No.: 173,209

[22] Filed: Dec. 22, 1993

[51] Int. Cl.$^6$ .......................... C12N 15/12; C07K 14/52
[52] U.S. Cl. .................. 435/69.1; 435/71.1; 435/240.1; 435/252.3; 435/320.1; 536/23.1; 536/23.5; 536/24.3; 536/24.31; 935/11; 935/22; 935/66; 935/72
[58] Field of Search .......................... 435/252.3, 69.1, 435/172.3, 69.5, 240., 320.1, 71.1; 536/23.1, 23.5, 24.3, 24.31; 935/4, 11, 22, 52, 66, 72

[56] References Cited

FOREIGN PATENT DOCUMENTS

WO9205198  4/1992  WIPO.

OTHER PUBLICATIONS

Clements, J. M. et al., Biological and Structural Properties of MIP-1 Alpha Expressed in Yeast, CytoKine, 4:76–82 (1992).

Graham, G. J. and Pragnell, I. B., SCI/MIP-1 Alpha: a Patent Stem Cell Inhibitor with Potential Roles in Development, Dev. Biol., 151:377–81 (1992).

Lukacs,. N. W., et al., The Role of MIP-1 Alpha in Schistosoma egg-induced granulomatous inflammation, J. Exp. Med., 177:1551–9 (1993).

Wolpe, S. D., and Cerami, A., MIPs 1 and 2: Members of a Novel Superfamily of Cytokins, FASEB J., 3:2565–73 (1989).

Primary Examiner—Stephen G. Walsh
Assistant Examiner—Prema Mertz
Attorney, Agent, or Firm—Elliot M. Olstein; Gregory D. Ferraro

[57] ABSTRACT

There is disclosed a human macrophage inflammatory protein-1 γ (MIP-1 γ) polypeptide and DNA(RNA) encoding such polypeptide. There is also provided a procedure for producing such polypeptide by recombinant techniques and for producing an antibody against such polypeptide. Another aspect of the invention provides a combination of the polypeptide of the present invention and a suitable pharmaceutical carrier for providing a therapeutically effective amount of the polypeptide for the treatment of various associated diseases.

32 Claims, 5 Drawing Sheets

```
TGAAGCTCCCACCAGGCCAGCTCTCCTCCCACAACAGCTTCCCACAGCATGAAGATCTCC
---------+---------+---------+---------+---------+---------+
                                                     M  K  I  S
GTGGCTGCAATTCCCTTCTTCCTCCTCATCACCATCGCCCTAGGGACCAAGACTGAATCC
---------+---------+---------+---------+---------+---------+
 V  A  A  I  P  F  F  L  L  I  T  I  A  L  G  T  K  T  E  S
TCCTCACGGGGACCTTACCACCCCTCAGAGTGCTGCTTCACCTACACTACCTACAAGATC
---------+---------+---------+---------+---------+---------+
 S  S  R  G  P  Y  H  P  S  E  C  C  F  T  Y  T  T  Y  K  I
CCGCGTCAGCGGATTATGGATTACTATGAGACCAACAGCCAGTGCTCCAAGCCCGGAATT
---------+---------+---------+---------+---------+---------+
 P  R  Q  R  I  M  D  Y  Y  E  T  N  S  Q  C  S  K  P  G  I
GTCTTCATCACCAAAAGGGGCCATTCCGTCTGTACCAACCCCAGTGACAAGTGGGTCCAG
---------+---------+---------+---------+---------+---------+
 V  F  I  T  K  R  G  H  S  V  C  T  N  P  S  D  K  W  V  Q
GACTATATCAAGGACATGAAGGAGAACTGAGTGACCCAGAAGGGGTGGCGAAGGCACAGC
---------+---------+---------+---------+---------+---------+
 D  Y  I  K  D  M  K  E  N  *
TCAGAGACATAAAGAGAAGATGCCAAGGCCCCCTCCTCCACCCACCGCTAACTCTCAGCC
---------+---------+---------+---------+---------+---------+
CCAGTCACCCTCTTGGAGCTTCCCTGCTTTGAATTAAAGACCACTCATGCTCTT
```

FIG. 1

```
12  LLITIALGTKTESSSRGPYHPSECCFTYTTYKIPRQRIMDYYETNSQCSKPGIVFITKRG  71
    LL T+AL  +  S+       P+ CCF+YT+ +IP+   I DY+ET+SQCSKP ++F+TKRG
11  LLCTMALCNQVLSAPLAADTPTACCFSYTSRQIPQNFIADYFETSSQCSKPSVIFLTKRG  70

72  HSVCTNPSDKWVQDYIKDMK  91
     VC +PS++WVQ Y+ D++
71  RQVCADPSEEWVQKYVSDLE  90
```

1 = Heart 2 = Hippocampus 3 = prostate 4 = spleen 5 = Lung
6 = liver 7 = kidney 8 = Gall Blader 9 = testis 10 = ovary

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 474 BASE PAIRS
        ( B ) TYPE: NUCLEIC ACID
        ( C ) STRANDEDNESS: SINGLE
        ( D ) TOPOLOGY: LINEAR     ( i i ) MOLECULE TYPE: cDNA     ( x i ) SEQUENCE DESCRIPTION: SEQ ID NO:1:

```
TGAAGCTCCC ACCAGGCCAG CTCTCCTCCC ACAACAGCTT CCCACAGCAT GAAGATCTCC      60
GTGGCTGCAA TTCCCTTCTT CCTCCTCATC ACCATCGCCC TAGGGACCAA GACTGAATCC     120
TCCTCACGGG GACCTTACCA CCCCTCAGAG TGCTGCTTCA CCTACACTAC CTACAAGATC     180
CCGCGTCAGC GGATTATGGA TTACTATGAG ACCAACAGCC AGTGCTCCAA GCCCGGAATT     240
GTCTTCATCA CCAAAAGGGG CCATTCCGTC TGTACCAACC CCAGTGACAA GTGGGTCCAG     300
GACTATATCA AGGACATGAA GGAGAACTGA GTGACCCAGA AGGGGTGGCG AAGGCACAGC     360
TCAGAGACAT AAAGAGAAGA TGCCAAGGCC CCCTCCTCCA CCCACCGCTA ACTCTCAGCC     420
CCAGTCACCC TCTTGGAGCT TCCCTGCTTT GAATTAAAGA CCACTCATGC TCTT           474
```

( 2 ) INFORMATION FOR SEQ ID NO:2:

( i ) SEQUENCE CHARACTERISTICS:
        ( A ) LENGTH: 93 AMINO ACIDS
        ( B ) TYPE: AMINO ACID
        ( C ) STRANDEDNESS:
        ( D ) TOPOLOGY: LINEAR     ( i i ) MOLECULE TYPE: PROTEIN     ( x i ) SEQUENCE DESCRIPTION: SEQ ID NO:2:

```
Met Lys Ile Ser Val Ala Ala Ile Pro Phe Phe Leu Leu Ile Thr
                -20              -15                      -10
Ile Ala Leu Gly Thr Lys Thr Glu Ser Ser Ser Arg Gly Pro Tyr
                 -5               1                        5
His Pro Ser Glu Cys Cys Phe Thr Tyr Thr Thr Tyr Lys Ile Pro
                10              15                       20
Arg Gln Arg Ile Met Asp Tyr Tyr Glu Thr Asn Ser Gln Cys Ser
            25              30                       35
Lys Pro Gly Ile Val Phe Ile Thr Lys Arg Gly His Ser Val Cys
                40              45                       50
Thr Asn Pro Ser Asp Lys Trp Val Gln Asp Tyr Ile Lys Asp Met
                55              60                       65
Lys Glu Asn
```

( 2 ) INFORMATION FOR SEQ ID NO:3:

(i) SEQUENCE CHARACTERISTICS:
  (A) LENGTH: 30 BASE PAIRS
  (B) TYPE: NUCLEIC ACID
  (C) STRANDEDNESS: SINGLE
  (D) TOPOLOGY: LINEAR (ii) MOLECULE TYPE: Oligonucleotide (xi) SEQUENCE DESCRIPTION: SEQ ID NO:3:

GCCCGCGGAT CCTCCTCACG GGGACCTTAC    30

(2) INFORMATION FOR SEQ ID NO:4:

(i) SEQUENCE CHARACTERISTICS:
  (A) LENGTH: 32 BASE PAIRS
  (B) TYPE: NUCLEIC ACID
  (C) STRANDEDNESS: SINGLE
  (D) TOPOLOGY: LINEAR (ii) MOLECULE TYPE: Oligonucleotide (xi) SEQUENCE DESCRIPTION: SEQ ID NO:4:

GCCTGCTCTA GATCAAAGCA GGGAAGCTCC AG    32

(2) INFORMATION FOR SEQ ID NO:5:

(i) SEQUENCE CHARACTERISTICS:
  (A) LENGTH: 80 AMINO ACIDS
  (B) TYPE: AMINO ACID
  (C) STRANDEDNESS:
  (D) TOPOLOGY: LINEAR (ii) MOLECULE TYPE: PROTEIN (xi) SEQUENCE DESCRIPTION: SEQ ID NO:5:

Leu Leu Cys Thr Met Ala Leu Cys Asn Gln Val Leu Ser Ala Pro
              5                   10                  15

Leu Ala Ala Asp Thr Pro Thr Ala Cys Cys Phe Ser Tyr Thr Ser
              20                  25                  30

Arg Gln Ile Pro Gln Asn Phe Ile Ala Asp Tyr Phe Glu Thr Ser
              35                  40                  45

Ser Gln Cys Ser Lys Pro Ser Val Ile Phe Leu Thr Lys Arg Gly
              50                  55                  60

Arg Gln Val Cys Ala Asp Pro Ser Glu Glu Trp Val Gln Lys Tyr
              65                  70                  75

Val Ser Asp Leu Glu
              80

POLYNUCLEOTIDE ENCODING MACROPHAGE INFLAMMATORY PROTEIN γ

This invention relates to newly identified polynucleotide sequences, polypeptides encoded by such sequences, the use of such polynucleotides and polypeptides, as well as the production of such polynucleotides and polypeptides. More particularly, the polypeptide of the present invention is human macrophage inflammatory protein-1 γ (MIP-1 γ). The invention also relates to inhibiting the action of such polypeptide.

Macrophage inflammatory proteins (MIPs) are proteins that are produced by certain mammalian cells, for example, macrophages and lymphocytes, in response to stimuli, such as gram-negative bacteria, lipopolysaccharide and concanavalin A. Thus, the MIP molecules may have diagnostic and therapeutic utility for detecting and treating infections, cancer, myelopoietic dysfunction, and auto-immune diseases.

Several groups have cloned what are likely to be the human homologs of MIP-1 α and MIP-1β. In all cases, cDNAS were isolated from libraries prepared against activated T-cell RNA.

The macrophage inflammatory proteins (MIP-1 α and MIP-1 β) have been shown to exhibit pro-inflammation properties. MIP-1 α can induce migration and activation of human eosinophils. In addition, the murine MIP-1 α has suppressive effects on human hematopoietic stem cell proliferation, while the murine MIP-1β can abrogate the inhibitory effect of MIP-1 α. Finally, MIP-1 proteins can be detected in early wound inflammation cells and have been shown to induce production of IL-1 and IL-6 from wound fibroblast cells.

MIP-1s are related to chemokines which have numerous functions related to inflammation or would healing, immunoregulation and in a number of disease conditions.

The definition of the bioactivities of MIP-1 has been extensively studied and has utilized native MIP-1 and very recently recombinant MIP-1 α and MIP-1 β. Purified native MIP-1 (comprising MIP-1 α and MIP-1 β polypeptides) causes acute inflammation when injected either subcutaneously into the footpads of mice or intracisternally into the cerebrospinal fluid of rabbits (Wolpe and Cerami, 1989, *FASEB J.* 3:2565). In addition to these pro-inflammatory properties of MIP-1, which may be direct or indirect, MIP-1 has been recovered during the early inflammatory phases of wound healing in an experimental mouse model employing sterile wound chambers (Fahey, et al., 1990, Cytokine, 2:92). For example, PCT application U.S. 9106489, filed by Chiron Corporation, discloses a DNA molecule which is active as a template for producing mammalian macrophage inflammatory proteins (MIPs) in yeast.

In accordance with one aspect of the present invention, there is provided a novel polypeptide which is a macrophage inflammatory protein-1 γ(MIP-1 γ), as well as analogs and derivatives thereof. The human macrophage inflammatory protein-1 γ of the present invention is of human origin.

In accordance with another aspect of the present invention, there is provided a polynucleotide DNA (or RNA) which encodes such polypeptide.

In accordance with yet a further aspect of the present invention, there is provided a process for producing such a polypeptide by recombinant techniques.

In accordance with yet a further aspect of the present invention, there is provided a process for utilizing such polypeptide, or DNA sequence encoding such polypeptide for therapeutic purposes, for example, immunoregulation including inflammatory activity, hematopoiesis and lymphocyte trafficking.

In accordance with yet a further aspect of the present invention, there is provided an antibody against such polypeptide. Such antibodies may be used in the treatment of arteriosclerosis, and other related diseases.

In accordance with yet another aspect of the present invention, there is provided a composition which is employed as an antagonist to such polypeptide, e.g., an antibody against such polypeptide which may be used to inhibit the action of such polypeptide, for example, in the treatment of arteriosclerosis and as an anti-inflammation drug.

These and other aspects of the present invention should be apparent to those skilled in the art from the teachings herein.

The following drawings are illustrative of embodiments of the invention and are not meant to limit the scope of the invention as encompassed by the claims.

Figure 1:
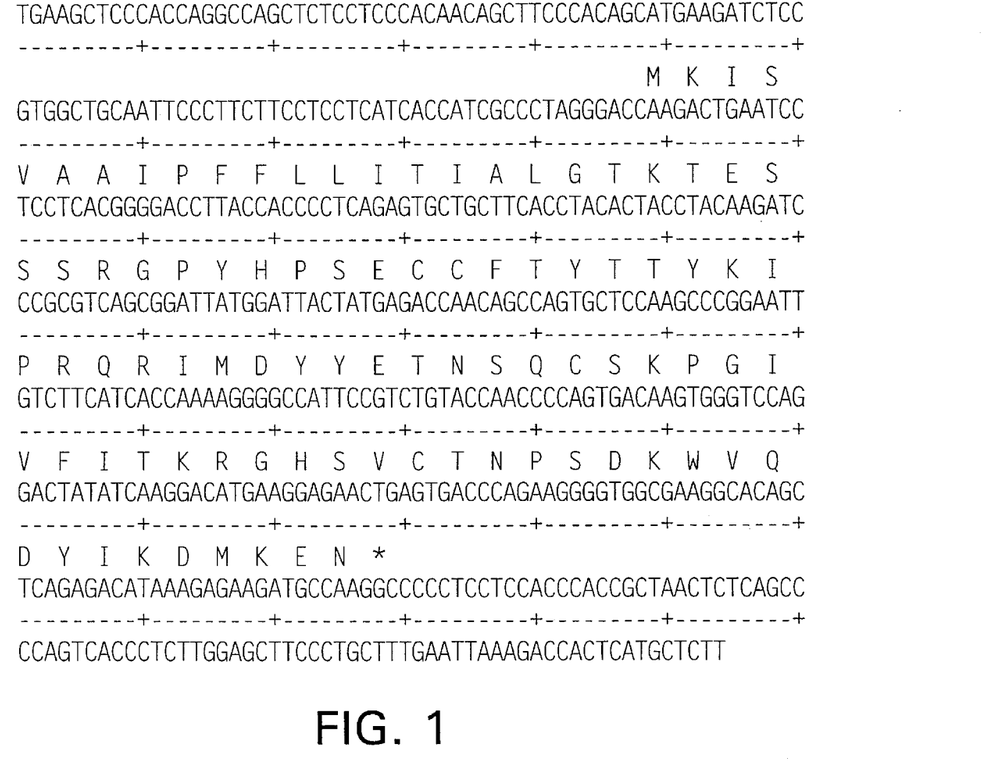
FIG. 1 displays the nucleotide sequence corresponding to the cDNAS of the MIP-1 γ and precursor protein sequence encoded by such polynucleotide sequence. In the precursor protein, the initial 24 amino acids represent the leader sequence.
Figure 2:
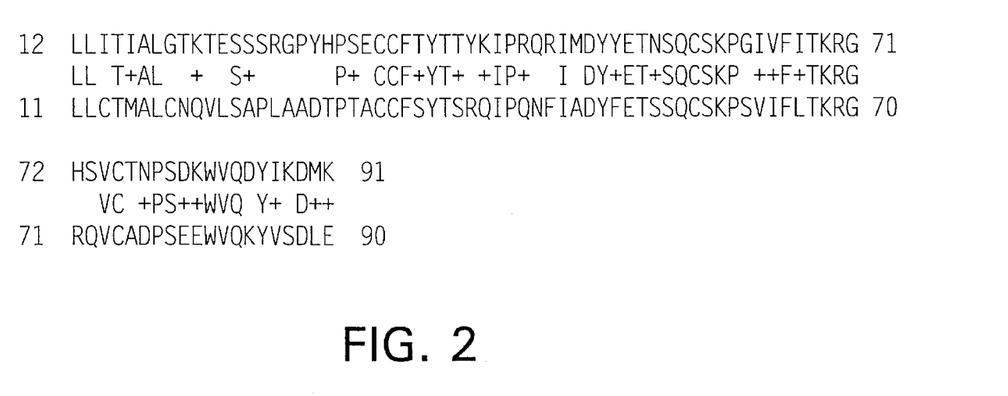
FIG. 2 displays two partial amino acid sequences of human MIP-1 proteins. The top sequence is human MIP-1 γ amino acid sequence and the bottom sequence is human MIP-1α (SEQ ID NO:5) [Human Tonsillar lymphocyte LD78 Beta protein precursor].

In accordance with one aspect of the present invention, there is provided a DNA sequence (and corresponding RNA sequence) as set forth in FIG. 1 (SEQ ID NO:1) of the drawings and/or DNA (RNA) sequences encoding the same polypeptide as shown in the sequence of FIG. 1 (SEQ ID NO:1) of the drawings, as well as fragment portions, derivatives, analogs and all allelic variants of such sequences.

In accordance with another aspect of the present invention, there is provided a polynucleotide which encodes the same polypeptide as the polynucleotide of the cDNA clone deposited as ATCC (American type Culture Collection, 12301 Parklawn Drive. Rockville, Md. 20852 USA) deposit number 75572, deposited on Oct. 13, 1993, and/or fragments, analogs, derivatives or allelic variants of such polynucleotide.

In the case of DNA, DNA may be single stranded or double stranded, and if single stranded the DNA sequence may be the "sense" strand shown in FIG. 1 (SEQ ID NO:1) or the one complementary thereto.

The polynucleotide (DNA or RNA, preferably DNA) includes at least the portion coding for the polypeptide, which coding portion may be the same as that in the deposited clone or may be different than that in the deposited clone provided that it encodes for the same polypeptide or an allelic variant thereof. The coding portion preferably encodes at least the mature form of the polypeptide of the present invention.

The present invention further relates to polynucleotide sequences which hybridize to the hereinabove-described sequences if there is at least 50% and preferably 70% identity between the sequences. In another preferred embodiment the present invention relates to polynucleotide sequences which hybridize under stringent conditions to the hereinabove-described polynucleotide sequences. As herein used, the term "stringent conditions" means hybridization will occur if there is at least 95% and preferably at least 97% identity between the segments. Thus, the present invention includes DNA (RNA) sequences encoding allelic variant forms of the peptide encoded by the DNA of FIG. 1 (SEQ ID NO:1). The DNA (RNA) is preferably provided in a purified and isolated form.

The present invention further relates to a polypeptide which is MIP-1 γ, and which, has the structure shown in FIG. 1 (SEQ ID NO:2), as well as allelic variants thereof, and analogs, fragments and derivatives thereof which have the same function as the naturally occurring polypeptide.

The present invention further relates to a polypeptide encoded by the DNA contained in the clone deposited as ATCC number 75572 on Oct. 13, 1993 as well as analogs, fragments, derivatives and allelic variants thereof. These deposits will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with description of sequences herein. A license may be required to make, use or sell the deposited materials, and no such license is hereby granted.

The polypeptide of the present invention is preferably provided in an isolated form, and preferably is purified.

The term "isolated" means that the material is removed from its original environment (e.g., the natural environment if it is naturally occurring). For example, a naturally-occurring polynucleotide or polypeptide present in a living animal is not isolated, but the same polynucleotide or DNA or polypeptide, separated from some or all of the coexisting materials in the natural system, is isolated. Such polynucleotide could be part of a vector and/or such polynucleotide or polypeptide could be part of a composition, and still be isolated in that such vector or composition is not part of its natural environment.

In a preferred embodiment, MIP-1 γ is a full length mature human polypeptide or an allelic or glycosylated variant thereof. The polynucleotide may also encode a preprotein which is processed and secreted from mammalian cells as the mature protein.

The polynucleotide sequence of the present invention may encode for a mature form of the MIP-1 γ. The polynucleotide sequence may also encode for a leader sequence. For example, the desired DNA sequence may be fused in the same reading frame to a DNA sequence which aids in expression and secretion of the polypeptide from the host cell, for example, a leader sequence which functions as a secretory sequence for controlling transport of the polypeptide from the cell. The protein having a leader sequence is a preprotein and may have the leader sequence cleaved by the host cell to form the mature form of the protein. The polynucleotide of the present invention may also be fused in frame to a marker sequence which allows for purification of the polypeptide of the present invention.

Thus, the polypeptide of the present invention may be the mature form of the MIP-1γ of the present invention; or may be in the form of a preprotein or prepolypeptide wherein the MIP-1γ includes a leader or secretory sequence; or may be in the form of a fusion protein wherein additional amino acids which aid in, for example, purification of the polypeptide are fused to the mature or preprotein at either the 3' or 5' end thereof.

In a preferred embodiment, the marker sequence is a hexahistidine tag supplied by a PQE-9 vector to provide for purification of the fusion protein in the case of a bacterial host or an HA tag when a mammalian host, e.g. COS-7 cells, are used.

The polypeptide of the present invention is located generally in many organs of the body. However, the polypeptide is found predominantly in the spleen, lung and ovary as shown by the Northern blot analysis of FIG. 5.

As hereinabove indicated, the present invention also includes variants of the polypeptide which is encoded by the DNA of FIG. 1 (SEQ ID NO:1) or and variants of the DNA contained in the deposited clone, which retains the qualitative activity of such a polypeptide which is MIP-1γ. The variant may be a substitutional variant, or an insertion variant or a deletional variant. Such variants can be naturally occurring allelic variants such as for example, those with different glycosylation patterns or substitution at the amino acid level or deletion at the amino acid level.

Such variants may also be produced by site specific mutagenesis. The substitutional variant may be a substituted conserved amino acid or a substituted non-conserved amino acid, and preferably a conserved amino acid.

A polynucleotide encoding a polypeptide of the present invention is structurally related to the pro-inflammatory supergene "intercrine" which is in the cytokine or chemokine family. It contains an open reading frame encoding a polypeptide of 93 amino acids precursors, which exhibits significant homology to a number of chemokines. Among the top matches are: 1) 48% identity and 72% similarity to the human macrophage inflammatory protein-α (MIP-1α) over a stretch of 80 amino acids; 2) 46% identity and 67% similarity to the mouse macrophage inflammatory protein 1-β (MIP-1 β) in a region of 82 amino acids. Furthermore, the four cysteine residues occurring in all chemokines in a characteristic motif are conserved in our clone. The fact that the first two cysteine residues in our gene are in adjacent positions classifies it as "C—C" or β subfamily of chemokines. In the other subfamily, the "CXC" or α subfamily, the first two cysteine residues are separated by one amino acid.

Host cells are transformed with the expression vectors of this invention and cultured in conventional nutrient media modified as appropriate for including in conventional nutrient media modified as appropriate for inducing promoters, selecting transformants or amplifying the MIP-1γ gene. The culture conditions, such as temperature, pH and the like, are those previously used with the host cell selected for expression, and will be apparent to the ordinarily skilled artisan.

"Transformation" means introducing DNA into an organisms so that the DNA is replicable, either as an extrachromosomal element or by chromosomal integration. Unless indicated otherwise, the method used herein for transformation of the host cells is the method of Graham, F. and van der Eb, A., *Virology* 52:456–457 (1973). However, other methods for introducing DNA into cells such as by nuclear injection or by protoplast fusion may also be used. If prokaryotic cells or cells which contain substantial cell wall constructions are used, the preferred method of transformation is calcium treatment using calcium chloride as described by Cohen, F. N., et al., *Proc. Natl. Acad. Sci.* (USA), 69:2110 (1972).

"Transfection" refers to the introduction of DNA into a host cell whether or not any coding sequences are ultimately expressed. Cells do not naturally take up DNA. Thus, a variety of technical "tricks" are utilized to bypass the natural barriers to gene transfer. Numerous methods of transfection are known to the ordinarily skilled artisan, for example, $CaPO_4$, electroporation and DEAE Dextran. (J. Sambrook, E. Fritsch, T. Maniatis, *Molecular Cloning: A Laboratory Manual*, Cold Spring Laboratory Press, 1989.) Transformation of the host cell is the indicia of successful transfection.

The polynucleotide of the present invention may be employed for producing a polypeptide by recombinant techniques. Thus, for example, the polynucleotide sequence may be included in any one of a variety of vectors or plasmids for expressing a polypeptide. Such vectors include chromosomal, nonchromosomal and synthetic DNA sequences, e.g., derivatives of SV40; bacterial plasmids; phage DNA's; yeast plasmids; vectors derived from combinations of plasmids and phage DNAs, viral DNA such as vaccinia, adenovirus, fowl pox virus, and pseudorabies. However, any other plasmid or vector may be used as long as they are replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli*. lac or trp, the phage lambda PL promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain a gene to provide a phenotypic trait for selection of transformed host cells such as dihydrofolate reductase or neomycin resistance for eukaryotic cell culture, or such as tetracycline or ampicillin resistance in *E. coli*.

Figure 3:
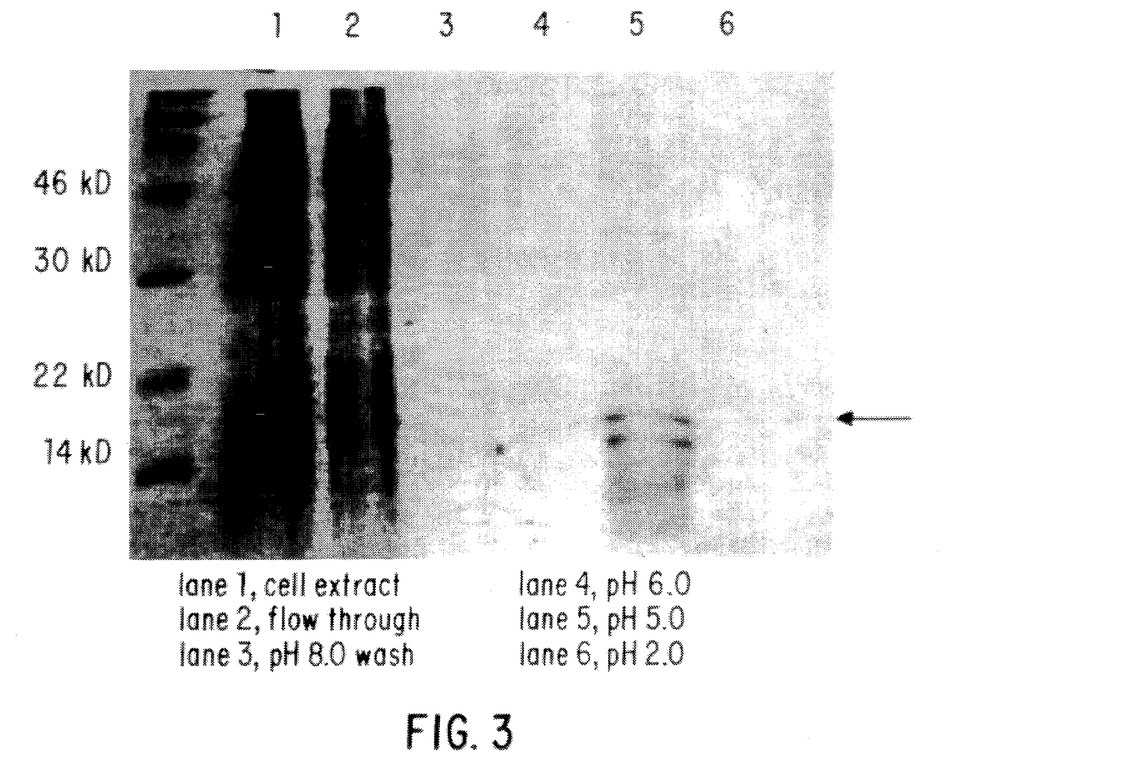
FIG. 3 shows the protein bands in Lane 5 corresponding to the MIP-1 γ protein after expression in a bacterial expression system and purification.
Figure 4:
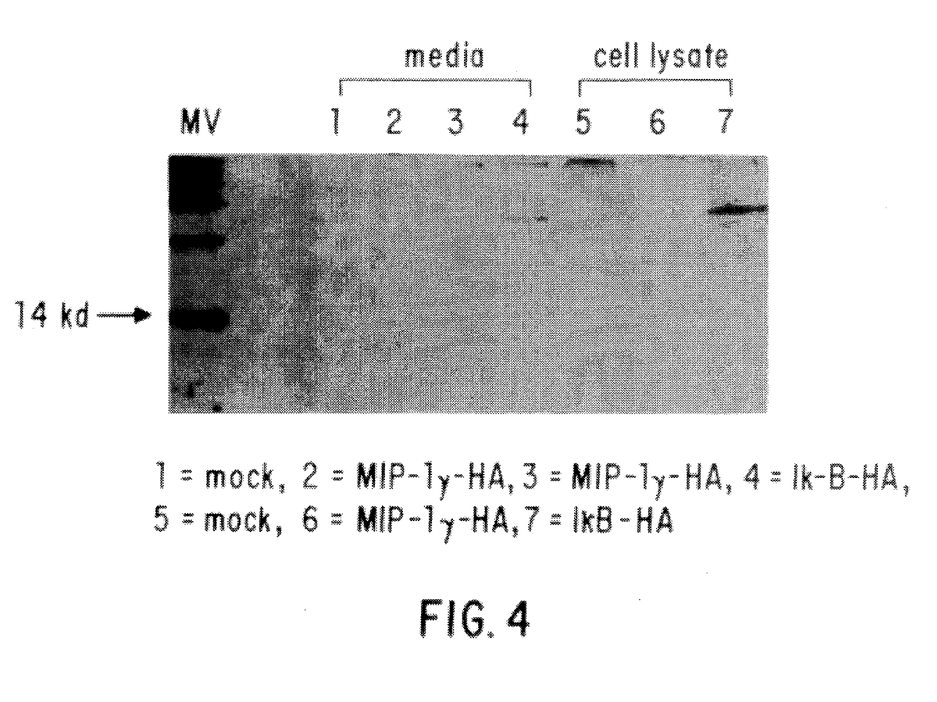
FIG. 4 shows the protein bands corresponding to COS cell expression of MIP-1 γ.

The vector containing the appropriate DNA sequence as hereinabove described, as well as an appropriate promoter or control sequence, may be employed to transform an appropriate host to permit the host to express the protein. The polypeptide of the present invention, MIP-1γ,as it is expressed from a bacterial expression system, e.g., *E. coli*, is shown in FIG. 3, Lane 5. The MIP-1γ as it is expressed when COS cells are used as the transforming cells is shown in FIG. 4, Lanes 2 and 3.

As representative examples of appropriate hosts, there may be mentioned: bacterial cells, such as *E. coli, Salmonella typhimurium*; fungal cells, such as yeast, animal cells such as CHO or Bowes melanoma; plant cells, etc. The selection of an appropriate host is deemed to be within the scope of those skilled in the art from the teachings herein.

As hereinabove indicated, the expression vehicle including the appropriate DNA sequence inserted at the selected site may include a DNA or gene sequence which is not part of the gene coding for the polypeptide. For example, the desired DNA sequence may be fused in the same reading frame to a DNA sequence which aids in expression or improves purification or permits expression of the appropriate protein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE-9 (Qiagen), pBS,pD10, phagescript, pSIX74, pBluescript SK, pBSKS, pNH8A, pNH16A, pNH18A, pNH46A (Stratagene); pTRC99A, pKK223-3, pKK233-3, pDR540, pRIT5 (Pharmacia); Eukaryotic: pWLNEO, pSV2CAT, pOG44, pXT1, pSG (Stratagene) pSVK3, pBPV, pMSG, pSVL (Pharmacia).

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, and trc. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described construct. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE, dextran mediated transfection, or electroporation. (Davis, L., Dibner, M., Battcy, I., *Basic Methods in Molecular Biology*, (1986)).

The constructs in host cells can be used in a conventional manner to produce the gene product coded by the recombinant sequence. Alternatively, the encoded polypeptide can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., *Molecular Cloning: A Laboratory Manual*, Second Edition, Cold Spring Harbor, N.Y., (1989), the disclosure of which is hereby incorporated by reference.

Transcription of the DNA encoding the polypeptide of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtills, Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Promoter regions can be selected from any desired gene using CAT (chloramphenicol transferase) vectors or other vectors with selectable markers. Two appropriate vectors are pKK232-8 and PCM7. Particular named bacterial promoters include lacI, lacZ, T3, T7, gpt, lambda $P_R$, and trc. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

Following transformation of a suitable host strain and growth of the host strain to an appropriate cell density, the selected promoter is derepressed by appropriate means (e.g., temperature shift or chemical induction) and cells are cultured for an additional period. Cells are typically harvested by centrifugation, disrupted by physical or chemical means, and the resulting crude extract retained for further purification.

MIP-1 γ is recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography (e.g. using DNA or nucleotides on a solid support), hydroxylapatite chromatography and lectin chromatography. It is preferred to have low concentrations (approximately 0.15–5 Mm) of calcium ion present during purification. (Price et al., *J. Biol. Chem.*, 244:917 (1969)).

Various mammalian cell culture systems can also be employed to express recombinant protein. Examples of mammalian expression systems include the COS-7 lines of monkey kidney fibroblasts, described by Gluzman, *Cell*, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

Recombinant protein produced in bacterial culture is usually isolated by initial extraction from cell pellets, followed by one or more salting-out, aqueous ion exchange or size exclusion chromatography steps. Protein refolding steps can be used, as necessary, in completing configuration of the mature protein. Finally, high performance liquid chromatography (HPLC) can be employed for final purification steps. Microbial cells employed in expression of proteins can be disrupted by any convenient method, including freeze-thaw cycling, sonication, mechanical disruption, or use of cell lysing agents, such methods are well know to those skilled in the art.

The polypeptide of the present invention may be a naturally purified product, or a product of chemical synthetic procedures, or produced by recombinant techniques from a prokaryotic or eukaryotic host (for example, by bacterial, yeast, higher plant, insect and mammalian cells in culture) of a polynucleotide sequence of the present invention. Depending upon the host employed in a recombinant production procedure, the polypeptides of the present invention may be glycosylated with mammalian or other eukaryotic carbohydrates or may be non-glycosylated. Polypeptides of the invention may also include an initial methionine amino acid residue (at position minus 1).

In addition to naturally occurring allelic forms of the polypeptide, the present invention also embraces analogs and fragments thereof, which also function as an inflammatory protein. Thus, for example, one or more of the amino acid residues of the polypeptide may be replaced by conserved amino acid residues.

The polypeptide of the present invention may be used in a variety of immunoregulatory and inflammatory functions and also in a number of disease conditions. MIP-1γ is a chemokine and therefore it is a chemo-attractant for leukocytes (such as monocytes, neutrophils, T lymphocytes, basophils, etc.). Accordingly, MIP-1γ can be used to facilitate wound healing since it would cause infiltration of target immune cells to the wound area.

Further, the polypeptide of the present invention may be useful in anti-tumor therapy since there is evidence that chemokine expressing cells injected into tumors have caused regression of the tumor, for example, in the treatment of kaposi sarcoma.

The polypeptide of the present invention is also useful in the treatment of stroke, thrombocytosis, pulmonary emboli and myeloproliferative disorders, since MIP-1γ increases vascular permeability.

The polypeptide of the present invention can be useful in protecting hematopoietic stem cells during chemotherapy.

The polypeptide may also be employed in accordance with the present invention by expression of such polypeptide in vivo, which is often referred to as "gene therapy."

Thus, for example, cells from a patient may be transduced with a polynucleotide (DNA or RNA) encoding the polypeptide ex vivo, with the transduced cells then being provided to a patient to be treated with the polypeptide. Such methods are well-known in the art. For example, cells may be transduced by procedures known in the art by use of a retroviral particle containing RNA encoding the polypeptide of the present invention.

Similarly, transduction of cells may be accomplished in vivo for expression of the polypeptide in vivo by, for example, procedures known in the art. As known in the art, a producer cell for producing a retroviral particle containing RNA encoding the polypeptide of the present invention may be administered to a patient for transduction in vivo and expression of the polypeptide in vivo. These and other methods for administering a polypeptide of the present invention by such method should be apparent to those skilled in the art from the teachings of the present invention. For example, the expression vehicle for transducing cells may be other than a retrovirus, for example, an adenovirus which may be used to transduce cells in vivo after combination with a suitable delivery vehicle.

The polypeptide of the present invention may be employed in combination with a suitable pharmaceutical carrier. Such compositions comprise a therapeutically effective amount of the protein, and a pharmaceutically acceptable carrier or excipient. Such a carrier includes but is not limited to saline, buffered saline, dextrose, water, glycerol, ethanol, and combinations thereof. The formulation should suit the mode of administration.

The MIP-1γ of the present invention may be prepared such that it may be injected into a patient. The injections are prepared by conventional methods, for example, using physiological saline or aqueous solutions containing glucose or other auxiliary agents. The pharmaceutical compositions, such as tablets and capsules, can also be prepared in accordance with conventional methods. The injections, solutions, tablets and capsules as the pharmaceutical compositions are prepared under aseptic conditions. The amount administered is a therapeutically effective amount, such as from about 1 μg/kg body weight to about 5 mg/kg body weight daily.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptide of the present invention may be employed in conjunction with other therapeutic compounds.

When the MIP-1 γ of the present invention is used as a pharmaceutical, it can be given to mammals, in a suitable vehicle, for example, in therapeutically effective doses of at least about 10 μg/kg body weight and in most cases it would be administered in an amount not in excess of about 8 mg/kg body weight per day, and preferably the dosage is from about 10 μg/kg body weight to about 1 mg/kg body weight, taking into account the routes of administration, symptoms, etc.

Each of the cDNA sequences identified herein or a portion thereof can be used in numerous ways as polynucleotide reagents. The sequences can be used as diagnostic probes for the presence of a specific mRNA in a par screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 500 or 600 bases; however, clones larger than 2,000 bp have a higher likelihood of binding to a unique chromosomal location with sufficient signal intensity for simple detection. FISH requires use of the clone from which the EST was derived, and the longer the better. For example, 2,000 bp is good, 4,000 is better, and more than 4,000 is probably not necessary to get good results a reasonable percentage of the time. For a review of this technique, see Verma et al., *Human Chromosomes: a Manual of Basic Techniques*, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb.

Comparison of affected and unaffected individuals generally involves first looking for structural alterations in the chromosomes, such as deletions or translocations that are visible from chromosome spreads or detectable using PCR based on that cDNA sequence. Ultimately, complete sequencing of genes from several individuals is required to confirm the presence of a mutation and to distinguish mutations from polymorphisms.

The present invention is further directed to inhibiting MIP-1γ in vivo to reduce and/or eliminate its inflammatory effect by use of antisense technology. Antisense technology can be used to control gene expression through triple-helix formation or antisense DNA or RNA, both of which methods are based on binding of a polynucleotide sequence to DNA or RNA. For example, the 5' coding portion of the polynucleotide sequence, which encodes for the polypeptide of the present invention, is used to design an antisense RNA oligonucleotide of from about 10 to 40 base pairs in length. A DNA oligonucleotide is designed to be complementary to a region of the gene involved in transcription (triple helix—see Lee et al., *Nucl. Acids Res.*, 6:3073 (1979); Cooney et al, *Science*, 241:456 (1988); and Dervan et al., *Science*, 251: 1360 (1991)), thereby preventing transcription and the production of MIP-1 γ.

The antisense RNA oligonucleotide hybridizes to the MRNA in vivo and blocks translation of the MRNA molecule into the MIP-1γ (antisense - Okano, *J. Neurochem.*, 56:560 (1991); *Oligodeoxynucleotides as Antisense Inhibitors of Gene Expression*, CRC Press, Boca Raton, FL (1988)).

Alternatively, the oligonucleotides described above can be delivered to cells by procedures in the art such that the antisense RNA or DNA may be expressed in vivo to inhibit production of MIP-1 γ in the manner described above.

Accordingly, antisense constructs to the MIP-1γ can be used to treat atherosclerosis, since MIP-1γ is secreted by arterial smooth muscle cells, thereby attracting macrophages. Atherosclerotic lesions known as fatty-streaks may be macrophage-derived.

The protein, its fragments or other derivatives, or analogs thereof, or cells expressing them can be used as an immunogen to produce antibodies thereto. These antibodies can be, for example, polyclonal, monoclonal, chimeric, single chain, Fab fragments, or the product of an Fab expression library. Various procedures known in the art may be used for the production of polyclonal antibodies.

Antibodies generated against the polypeptide corresponding to a sequence of the present invention can be obtained by direct injection of the polypeptide into an animal or by administering the polypeptide to an animal, preferably a nonhuman. The antibody so obtained will then bind the polypeptide itself. In this manner, even a sequence encoding only a fragment of the polypeptide can be used to generate antibodies binding the whole native polypeptide. Such antibodies can then be used to isolate the polypeptide from tissue expressing that polypeptide. Moreover, a panel of such antibodies, specific to a large number of polypeptides, can be used to identify and differentiate such tissue.

For preparation of monoclonal antibodies, any technique which provides antibodies produced by continuous cell line cultures can be used. Examples include the hybridoma technique (Kohler and Milstein, 1975, *Nature*, 256:495–497), the trioma technique, the human B-cell hybridoma technique (Kozbor et al., 1983, *Immunology Today* 4:72), and the EBV-hybridoma technique to produce human monoclonal antibodies (Cole, et al., 1985, in *Monoclonal Antibodies and Cancer Therapy*, Alan R. Liss, Inc., pp. 77–96).

Techniques described for the production of single chain antibodies (U.S. Pat. No. 4,946,778) can be adapted to produce single chain antibodies to immunogenic polypeptide products of this invention.

Antibodies specific to the polypeptide of the present invention may further be used as antagonists to inhibit the proper functioning of the polypeptide. In this manner, the antibodies may be used as an anti-inflammation drug, by preventing the attraction of leukocytes to a wound area. Antibodies specific to MIP-1 γ would also be useful for treating atherosclerosis.

Alternatively, an antagonist to the polypeptide of the present invention may be employed which binds to the receptors to which the polypeptide of the present invention normally binds. The antagonist is similar to an inactive form of the polypeptide and may be generated in ways similar to the ways in which antibodies specific to MIP-1γ are generated. In this way, the action of the MIP-1γ is prevented and the antagonist may be used as an anti-inflammation drug. The antagonist may operate in a similar way to be used to treat atherosclerosis since the antagonist will bind to the receptors of MIP-1γ and therefore macrophages will not be attracted to the arterial walls.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially-available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using percent polyacrylamide gel described by Goeddel, D. et al., *Nucleic Acids Res.*, 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiaster bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 μg of approximately equimolar amounts of the DNA fragments to be ligated.

EXAMPLE 1

Bacterial Expression and Purification of MIP-1γ

Figure 6:
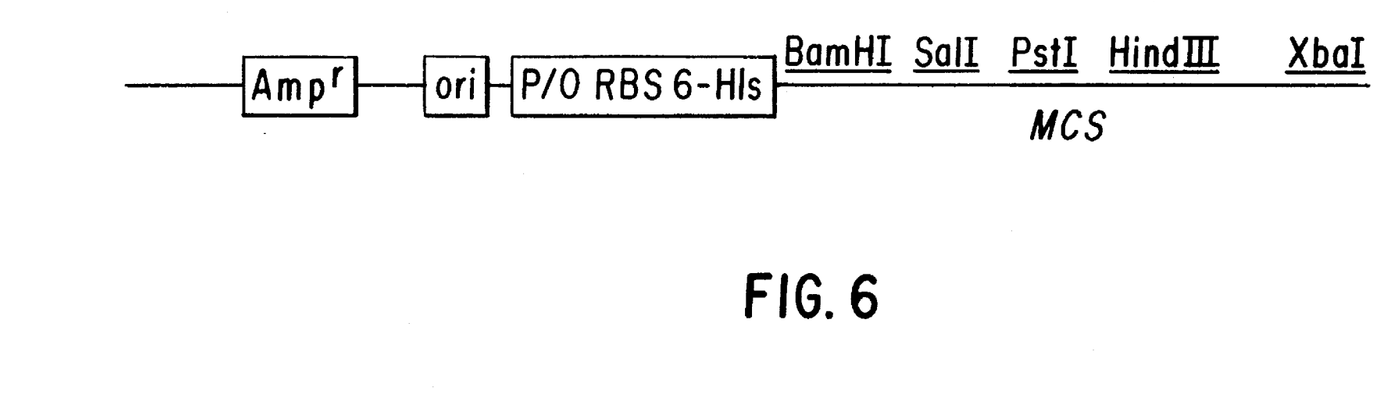
FIG. 6 is a schematic representation of the pQE-9 vector.

The DNA sequence encoding for MIP-1γ, pBLSKMIP (ATCC #75572) is initially amplified using PCR oligonucleotide primers corresponding to the 5' and 3' sequences of the processed MIP-1γ protein (minus the signal peptide sequence) and additional nucleotides corresponding to Bam HI and XbaI were added to the 5' and 3' sequences respectively. The 5' oligonucleotide primer has the sequence GCCCGCGGATCCTCCTCACGGGGACCTTAC (SEQ ID NO:3) contains a BamHI restriction enzyme site followed by 15 nucleotides of MIP-1γ coding sequence starting from the presumed terminal amino acid of the processed protein codon; The 3' sequence GCCTGCTCTAGATCAAAG-CAGGGAAGCTCCAG (SEQ ID NO:4) contains complementary sequences to XbaI site a translation stop codon and the last 20 nucleotides of MIP-1γ coding sequence. The restriction enzyme sites correspond to the restriction enzyme sites on the bacterial expression vector pQE-9. (Qiagen, Inc. 9259 Eton Avenue, Chatsworth, Calif., 91311). pQE-9 encodes antibiotic resistance (Amp$^r$), a bacterial origin of replication (ori), an IPTG-regulatable promoter operator (P/O), a ribosome binding site (RBS), a 6-His tag and restriction enzyme sites. pQE-9 was then digested with BamHI and XbaI. The amplified sequences were ligated into pQE-9 and were inserted in frame with the sequence encoding for the histidine tag and the RBS. FIG. 6 shows a schematic representation of this arrangement. The ligation mixture was then used to transform E. coli strain available from Qiagen under the trademark M15/rep 4. M15/rep4 contains multiple copies of the plasmid pREP4, which expresses the lacI repressor and also confers kanamycin resistance (Kan$^r$). Transformants are identified by their ability to grow on LB plates and ampicillin/kanamycin resistant colonies were selected. Plasmid DNA was isolated and confirmed by restriction analysis. Clones containing the desired constructs were grown overnight (O/N) in liquid culture in LB media supplemented with both Amp (100 ug/ml) and Kan (25 ug/ml). The O/N culture is used to inoculate a large culture at a ratio of 1:100 to 1:250. The cells were grown to an optical density 600 (O.D.$^{600}$) of between 0.4 and 0.6. IPTG ("Isopropyl-B-D-thiogalacto pyranoside") was then added to a final concentration of 1 mM. IPTG induces by inactivating the lacI repressor, clearing the P/O leading to increased gene expression. Cells were grown an extra 3 to 4 hours. Cells were then harvested by centrifugation. The cell pellet was solubilized in the chaotropic agent 6 Molar Guanidine HCl. After clarification, solubilized MIP-1γ was purified from this solution by chromatography on a Nickel-Chelate column under conditions that allow for tight binding by proteins containing the 6-His tag. Hochuli, E. et al., *J. Chromatography* 411:177–184 (1984). MIP-1γ (95% pure) was eluted from the column in 6 molar guanidine HCl pH 5.0 and for the purpose of renaturation adjusted to 3 molar guanidine HCl, 100 mM sodium phosphate, 10 mmolar glutathione (reduced) and 2 mmolar glutathione (oxidized). After incubation in this solution for 12 hours the protein was dialyzed to 10 mmolar sodium phosphate. The presence of a new protein corresponding to 14 kd following induction demonstrated expression of the MIP-1γ (FIG. 3).

EXAMPLE 2

Expression of Recombinant MIP-1γ in COS Cells

The expression of plasmid, CMV-MIP-1 γ HA is derived from a vector pcDNAI/Amp (Invitrogen) containing: 1) SV40 origin of replication, 2) ampicillin resistance gens, 3) E. coli replication origin, 4) CMV promoter followed by a polylinker region, a SV40 intron and polyadenylation site. A DNA fragment encoding the entire MIP-1 γ precursor and a HA tag fused in frame to its 3' end was cloned into the polylinker region of the vector, therefore, the recombinant protein expression is directed under the CMV promoter. The HA tag correspond to an epitope derived from the influenza hemagglutinin protein as previously described (I. Wilson, H. Niman, R. Heighten, A Cherenson, M. Connolly, and R. Lerner, 1984, Cell 37, 767). The infusion of HA tag to our target protein allows easy detection of the recombinant protein with an antibody that recognizes the HA epitope.

The plasmid construction strategy is described as follows:

The DNA sequence, pBLSKMIP (ATCC # 75572), encoding for MIP-1γ was constructed by PCR on the original EST cloned using two primers: the 5' primer (5'GGAAAGCT-TATGAAGATTCCGTGGCTGC-3') contains a HindIII site followed by 20 nucleotides of MIP-1 γ coding sequence starting from the initiation codon; the 3' sequence (5'-CGCTCTAGATCAAGCGTAGTCTGGGACGTCGTAT GGGTAGTTCTCCTTCATGTCCTTG-3') contains complementary sequences to Xba I site, translation stop codon, HA tag and the last 19 nucleotides of the MIP-1 γ coding sequence (not including the stop codon). Therefore, the PCR product contains a HindIII site, MIP-1 γ coding sequence followed by HA tag fused in frame, a translation termination stop codon next to the HA tag, and an XbaI site. The PCR amplified DNA fragment and the vector, pcDNAI/Amp, were digested with HindIII and XbaI restriction enzyme and ligated. The ligation mixture was transformed into E. coli strain SURE (available from Stratagens Cloning Systems, 11099 North Torrey Pines Road, La Jolla, Calif. 92037) the transformed culture was plated on ampicillin media plates and resistant colonies were selected. Plasmid DNA was isolated from transformants and examined by restriction analysis for the presence of the correct fragment. For expression of the recombinant MIP-1γ, COS cells were transfected with the expression vector by DEAE-DEXT-RAN method. (J. Sambrook, E. Fritsch, T. Maniatis, *Molecular Cloning: A Laboratory Manual*, Cold Spring Laboratory Press, (1989)). The expression of the MIP-1 γ-HA protein was detected by radiolabelling and immunoprecipitation method. (E. Harlow, D. Lane, *Antibodies: A Laboratory Manual*, Cold Spring Harbor Laboratory Press, (1988)). Cells were labelled for 8 hours with $^{35}$-cysteine two days post transfection. Culture media were then collected and cells were lysed with detergent (RIPA buffer (150 mM NaCl 1% NP-40, 0.1% SDS, 1% NP-40, 0.5% DOC, 50 mM Tris, pH 7.5). (Wilson, I. et al., Id. 37:767 (1984)). Both cell lysate and culture media were precipitated with a HA specific monoclonal antibody. Proteins precipitated were analyzed on 15% SDS-PAGE gels.

EXAMPLE 3

Expression pattern of MIP-17 in Human Tissue

Figure 5:
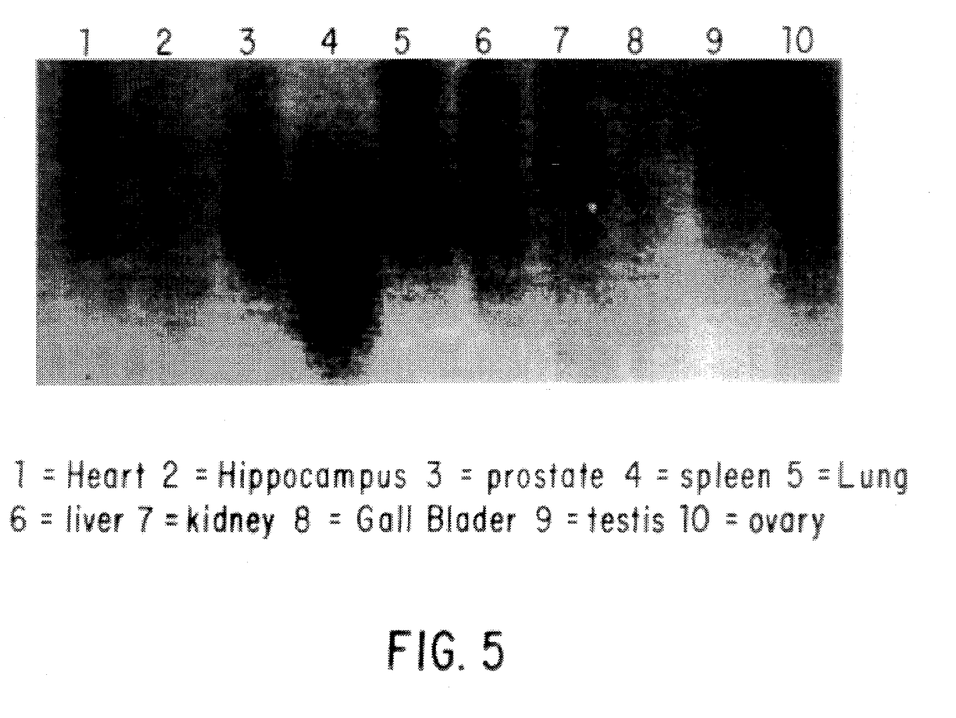
FIG. 5 is a northern blot analysis of the MIP-1 γ indicating the tissues in which this protein is most commonly found, namely, the spleen, lung and liver.

Northern blot analysis was carried out to examine the levels of expression of MIP-1γ in human tissues. Total cellular RNA samples were isolated with RNAzol™ B system (Biotecx Laboratories, Inc. 6023 South Loop East, Houston, Tex. 77033). About 10 ug of total RNA isolated from each human tissue specified was separated on 1% agarose gel and blotted onto a nylon filter. (Sambrook, Fritsch, and Maniatis, *Molecular Cloning*, Cold Spring Harbor Press, (1989)). The labeling reaction was done according to the Stratagene Prime-It kit with 50 ng DNA fragment. The labeled DNA was purified with a Select-G-50 column. (5 Prime-3 Prime, Inc. 5603 Arapahoe Road, Boulder, Colo. 80303). The filter was then hybridized with radioactive labeled full length MIP-1γ gene at 1,000,000 cpm/ml in 0.5 M NaPO$_4$, pH 7.4 and 7% SDS overnight at 65° C. After washing twice at room temperature and twice at 60° C. with 0.5×SSC, 0.1% SDS, the filter was then exposed at −70° C. overnight with an intensifying screen. The messeger RNA for MIP-1γ is abundant in spleen, lung, liver and less so in other tissues. (FIG. 5).

Numerous modifications and variations of the present invention are possible in light of the above teachings and, therefore, within the scope of the appended claims, the invention may be practiced otherwise than as particularly described.

---

What is claimed is:

1. An isolated polynucleotide comprising a polynucleotide having at least a 95% identity to a member selected from the group consisting of:
   (a) a polynucleotide encoding a polypeptide comprising the amino acid sequence as set forth in SEQ ID NO:2;
   (b) a polynucleotide encoding a polypeptide comprising amino acid 1 to amino acid 69 as set forth in SEQ ID NO:2; and
   (c) a polynucleotide which is complementary to the polynucleotide of (a) or (b).

2. The polynucleotide of claim 1 encoding a polypeptide comprising the amino acid sequence as set forth in SEQ ID NO:2.

3. The polynucleotide of claim 1 encoding a polypeptide comprising amino acid 1 to amino acid 69 as set forth in SEQ ID NO:2.

4. The polynucleotide of claim 1 comprising from nucleotide 1 to nucleotide 474 as set forth in SEQ ID NO:1.

5. The polynucleotide of claim 1 comprising from nucleotide 121 to nucleotide 474 as set forth in SEQ ID NO:1.

6. The polynucleotide of claim 1 comprising from nucleotide 121 to nucleotide 327 as set forth in SEQ ID NO:1.

7. The polynucleotide of claim 1 wherein the polynucleotide is a cDNA or genomic DNA.

8. The polynucleotide of claim 1 wherein the polynucleotide is mRNA.

9. An isolated polynucleotide comprising a polynucleotide having at least a 95% identity to a member selected from the group consisting of:
   (a) a polynucleotide encoding a mature polypeptide encoded by the DNA contained in ATCC Deposit No. 75572;
   (b) a polynucleotide encoding a polypeptide expressed by the DNA contained in ATCC Deposit No. 75572; and (c) a polynucleotide which is complementary to the polynucleotide of (a) or (b).

10. The polynucleotide of claim 9 wherein the polynucleotide encodes a mature polypeptide encoded by the DNA contained in ATCC Deposit No. 75572.

11. A vector containing the polynucleotide of claim 1.

12. A vector containing the polynucleotide of claim 2.

13. A vector containing the polynucleotide of claim 3.

14. A vector containing the polynucleotide of claim 4.

15. A vector containing the polynucleotide of claim 5.

16. A vector containing the polynucleotide of claim 6.

17. A vector containing the polynucleotide of claim 10.

18. A host cell transformed with the polynucleotide of claim 1.

19. A host cell transformed with the polynucleotide of claim 2.

20. A host cell transformed with the polynucleotide of claim 3.

21. A host cell transformed with the polynucleotide of claim 4.

22. A host cell transformed with the polynucleotide of claim 5.

23. A host cell transformed with the polynucleotide of claim 6.

24. A host cell transformed with the polynucleotide of claim 10.

25. A process for producing a polypeptide comprising:
in a host cell according to claim 18 expressing the polypeptide encoded by said polynucleotide; and
recovering said expressed polypeptide.

26. A process for producing a polypeptide comprising:
in a host cell according to claim 19 expressing the polypeptide encoded by said polynucleotide; and
recovering said expressed polypeptide.

27. A process for producing a polypeptide comprising:
in a host cell according to claim 20 expressing the polypeptide encoded by said polynucleotide; and
recovering said expressed polypeptide.

28. A process for producing a polypeptide comprising:
in a host cell according to claim 21 expressing the polypeptide encoded by said polynucleotide; and
recovering said expressed polypeptide.

29. A process for producing a polypeptide comprising:
in a host cell according to claim 22 expressing the polypeptide encoded by said polynucleotide; and
recovering said expressed polypeptide.

30. A process for producing a polypeptide comprising:
in a host cell according to claim 23 expressing the polypeptide encoded by said polynucleotide; and
recovering said expressed polypeptide.

31. A process for producing a polypeptide comprising:
in a host cell according to claim 24 expressing the polypeptide encoded by said polynucleotide; and
recovering said expressed polypeptide.

32. An isolated polynucleotide comprising a member selected from the group consisting of a polynucleotide encoding MIP-1γ comprising amino acid 1 to amino acid 69 as shown in SEO ID NO:2 and a polynucleotide encoding naturally occurring allelic variants thereof.

* * * * *